United States Patent
Fukushima et al.

(10) Patent No.: US 8,007,942 B2
(45) Date of Patent: *Aug. 30, 2011

(54) ION-DISSOCIATIVE FUNCTIONAL COMPOUND, METHOD FOR PRODUCTION THEREOF, IONIC CONDUCTOR, AND ELECTROCHEMICAL DEVICE

(75) Inventors: Kazuaki Fukushima, Kanagawa (JP); Shuichi Takizawa, Kanagawa (JP); Koichiro Hinokuma, Kanagawa (JP); Atsushi Nishimoto, Kanagawa (JP); Kazuhiro Noda, Kanagawa (JP)

(73) Assignee: Sony Corporation, Tokyo (JP)

( * ) Notice: Subject to any disclaimer, the term of this patent is extended or adjusted under 35 U.S.C. 154(b) by 1420 days.

This patent is subject to a terminal disclaimer.

(21) Appl. No.: 10/567,283

(22) PCT Filed: Aug. 4, 2004

(86) PCT No.: PCT/JP2004/011528
§ 371 (c)(1),
(2), (4) Date: Feb. 3, 2006

(87) PCT Pub. No.: WO2005/012239
PCT Pub. Date: Feb. 10, 2005

(65) Prior Publication Data
US 2009/0004525 A1   Jan. 1, 2009

(30) Foreign Application Priority Data

Aug. 4, 2003 (JP) .................. P2003-286228
Oct. 22, 2003 (JP) .................. P2003-361440

(51) Int. Cl.
*H01M 6/18* (2006.01)
*H01M 8/10* (2006.01)
*C07C 313/00* (2006.01)

(52) U.S. Cl. .............. 429/306; 977/735; 562/125

(58) Field of Classification Search ............. None
See application file for complete search history.

(56) References Cited

U.S. PATENT DOCUMENTS
6,890,676 B2 * 5/2005 Nuber et al. .......... 429/33
(Continued)

FOREIGN PATENT DOCUMENTS
JP    2002-063918    2/2002
(Continued)

OTHER PUBLICATIONS

DesMarteau et al. Journal of Fluorine Chemistry, 72(1995), 203-208.*

(Continued)

*Primary Examiner* — Melvin C Mayes
*Assistant Examiner* — Yun Qian
(74) *Attorney, Agent, or Firm* — K&L Gates LLP

(57) ABSTRACT

Disclosed herein are an ion-dissociative functional compound, a method for production thereof, an ionic conductor, and an electrochemical device, the ion-dissociative functional compound being thermally and chemically stable under the condition required of fuel cells and being suitable for use as a material such as protonic conductor in fuel cells. The proton-dissociative functional compound shown in FIG. 1A is composed of a fullerene $C_{60}$ molecule and about 10 sulfonic acid groups —$SO_3H$ as proton-dissociative groups each attached to the fullerene through a difluoromethane group —$CF_2$—. The proton-dissociative functional compound shown in FIG. 1B is composed of fullerene molecules three-dimensionally connected to each other through a linking group —$CF_2SO_2NHSO_2CF_2$—. It contains, as the proton-dissociative group, sulfoneimide groups —$SO_2NHSO_2$— and sulfoneamide groups —$SO_2H_2$ in addition to sulfonic acid groups. These compounds are prepared by introduction of difluoro(fluorosulfonyl)methyl groups into fullerene molecules, and ensuing imidization and hydrolysis.

2 Claims, 3 Drawing Sheets

U.S. PATENT DOCUMENTS

| | | |
|---|---|---|
| 7,008,713 B2 | 3/2006 | Nuber et al. |
| 2004/0062971 A1 | 4/2004 | Nuber |
| 2004/0115501 A1 | 6/2004 | Hinokuma et al. |
| 2009/0105357 A1* | 4/2009 | Hinokuma et al. ............ 521/29 |

FOREIGN PATENT DOCUMENTS

| | | |
|---|---|---|
| JP | 2002-075420 | 3/2002 |
| JP | 2002-193681 | 7/2002 |
| JP | 2002-193861 | 7/2002 |
| JP | 2003-086022 | 3/2003 |
| JP | 2003-123790 | 4/2003 |
| JP | 2003-123793 | 4/2003 |
| JP | 2003-187636 | 7/2003 |
| JP | 2003-303513 | 10/2003 |
| JP | 2003303513 | 10/2003 |
| WO | WO 01/06519 | 1/2001 |

OTHER PUBLICATIONS

Japanese Office Action issued on Feb. 19, 2009, for corresponding Japanese Patent Application JP 2003-361440.

Chen Qing-Yuu in ACTA. Chimica. Sinica., 48(1990), 596.

N.D. Volkov et al., "Preparation of Halodifluoromethanesulfonic Acid Derivatives," Synthesis, Dec. 1979, pp. 972-975.

* cited by examiner

ION-DISSOCIATIVE FUNCTIONAL COMPOUND, METHOD FOR PRODUCTION THEREOF, IONIC CONDUCTOR, AND ELECTROCHEMICAL DEVICE

CROSS REFERENCE TO RELATED APPLICATIONS

The present application claims priority to Japanese Patent Document Nos. P2003-286228 filed on Aug. 4, 2003 and P2003-361440 filed on Oct. 22, 2004, the disclosures of which are herein incorporated by reference.

The present invention relates to an ion-dissociative functional compound, a method for production thereof, an ionic conductor, and an electrochemical device, the ion-dissociative functional compound being suitable for use as a material (such as protonic conductor) in fuel cells.

Fuel cells of solid polymer electrolyte type commonly employ Nafion as the protonic conductor. Nafion is a perfluorosulfonic acid resin available from DuPont. It is a perfluorinated sulfonic acid polymer resin having the structure represented by the chemical formula 11 below.

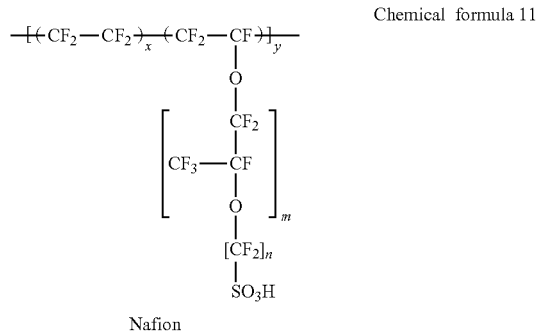

Nafion

Chemical formula 11

The molecular structure of Nafion is composed of two moieties with essentially different characteristic properties. One moiety is a perfluorinated single main chain constituting the hydrophobic molecular skeleton. The other is a perfluorinated side chain which contains a hydrophilic sulfonic acid group and functions as the proton donor site. The perfluorinated structure without unsaturated bonds is favorable to thermal and chemical stability. However, Nafion tends to decrease in protonic conductivity because it loses its adsorbed water (necessary for protonic conductivity) in a dry atmosphere or at a high temperature.

The present applicant disclosed a material capable of protonic conduction in the solid structure, in which the major constituent is a carbon cluster derivative composed of carbon cluster such as fullerene and proton-dissociative groups, such as hydrogensulfate ester groups ($-OSO_2OH$) and sulfonic acid groups ($-SO_2OH$), introduced thereinto. (See WO 01/06519, pp. 6-13, FIGS. 1, 2, 8, 9 and 10, mentioned later.) The present applicant also disclosed those compounds (shown in FIGS. 3A to 3D) as fullerene derivatives capable of protonic conduction. (See Japanese Patent Application No. 2002-28642.) The proton-dissociative groups may be attached directly to the fullerene nucleus as shown in FIGS. 3A and 3B or indirectly to the fullerene nucleus through a variety of spacer group as shown in FIGS. 3C and 3D. These compounds have a proton conductivity higher than $10^{-2}$ S/cm when there is an optimum amount of water in the solid structure.

Incidentally, the term "proton-dissociative group" as used above denotes any functional group having a hydrogen atom that ionizes to form a proton ($H^+$) and release itself from it. This definition is applied to the present invention.

Also, in the present invention, the term "ion-dissociative group" denotes any functional group that releases a metal ion. Moreover, the "functional group" includes not only any atomic group with only one bonding hand but also any atomic group with more than one bonding hand. The "functional group" may be present either at the terminal of the molecule or in the chain of the molecule.

Unfortunately, the fullerene-based materials shown in FIGS. 3A to 3D have several shortcomings. One of them is insufficient resistance to heat and/or chemical decomposition. The material shown in FIG. 3A is vulnerable to hydrolysis. The materials shown in FIGS. 3B to 3D are still poor in heat resistance despite their improved hydrolysis resistance. This is illustrated by the fact that butyl-connected fullerenosulfonic acid shown in FIG. 3C begins to decompose at about 100° C. upon heating.

Any material used for electrochemical devices, such as fuel cells, is essentially required to have good thermal and chemical stability under their operating conditions.

SUMMARY

The object of the present invention, which was completed in view of the foregoing, is to provide an ion-dissociative functional compound which has good thermal and chemical stability required of electrochemical devices under their operating conditions and is suitable for use as the protonic conductor of fuel cells, a method for production thereof, an ionic conductor which has high ionic conductivity as well as good thermal and chemical stability required of electrochemical devices under their operating conditions, and an electrochemical device with the ionic conductor.

The present invention is directed to an ion-dissociative functional compound represented by the chemical formula 1 below, a first ionic conductor containing the ion-dissociative functional compound, and a first method for producing the ion-dissociative functional compound, the method having a step of reacting $C_m$ (where m is a natural number for carbon atoms to form a spherical carbon molecule) with $I-CF_2-SO_2F$ to give $C_m-(CF_2-SO_2F)_n$ (where n is a natural number).

$$C_m-(CF_2\text{-Gp1})_n \qquad \text{Chemical formula 1}$$

(where, m is a natural number for carbon atoms to form a spherical carbon molecule; n is a natural number; and Gp1 denotes an ion-dissociative group.)

The present invention is directed also to an ion-dissociative functional compound having the linkage represented by the chemical formula 4 below, and a second method for producing the ion-dissociative functional compound, the method having a step of reacting $C_m$ with $I-CF_2-SO_2F$ to give $C_m-(CF_2-SO_2F)_n$ (where n is a natural number) and a step of reacting the $C_m-(CF_2-SO_2F)_n$ with a compound represented by the chemical formula 5 below.

$$C_m-CF_2\text{-Gp2-}CF_2-C_m \qquad \text{Chemical formula 4}$$

(where, m is a natural number for carbon atoms to form a spherical carbon molecule; and Gp2 denotes an ion-dissociative group.)

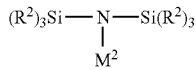

Chemical formula 5

(where $M^2$ denotes an alkali metal atom or $-Si(R^2)_3$, and $R^2$ denotes an alkyl group.)

The present invention is directed also to a second ionic conductor and an electrochemical device. The second ionic conductor is composed of a fullerene derivative in which the difluoromethylene group attaching to the ion-dissociative group (Gp1) attaches to the fullerene molecule. The electrochemical device is constructed such that the ionic conductor is held between the first and second electrodes so that it conducts ions from the first electrode to the second electrode.

Additional features and advantages of the present invention are described in, and will be apparent from, the following Detailed Description and the Figures.

DETAILED DESCRIPTION

Figure 1A:
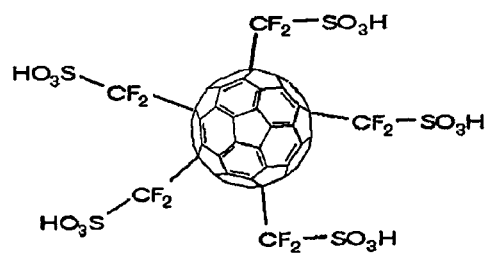
FIGS. 1A and 1B are schematic diagrams showing the structure of the proton-dissociative functional compound according to a preferred embodiment of the present invention.

The ion-dissociative functional compound according to the present invention requires that the spherical carbon molecule ($C_m$) be a fullerene molecule. In addition, the ion-dissociative group should be any one of proton-dissociative ones selected from the group consisting of hydrogensulfate ester group ($-OSO_2OH$), sulfonic acid group ($-SO_2OH$), dihydrogen phosphate ester group ($-OPO(OH)_2$), hydrogen phosphate ester group ($-OPO(OH)-$), phosphono group ($-PO(OH)_2$), carboxyl group ($-COOH$), sulfoneamide group ($-SO_2-NH_2$), sulfoneimide group ($-SO_2-NH-SO_2-$), methanedisulfonyl group ($-SO_2-CH_2-SO_2-$), carboxamide group ($-CO-NH_2$), and carboximide group ($-CO-NH-CO-$). These functional groups contain hydrogen that readily releases itself in the form of proton. Therefore, they are the desirable proton-dissociative functional groups.

The functional groups as represented above are proton-dissociative ones; however, they may have the hydrogen ion replaced by a cation, so that they function as ion-dissociative ones to release the cation. The cations may be those of alkali metal atoms. They are exemplified by lithium ions, sodium ions, potassium ions, rubidium ions, and cesium ions.

According to the present invention, the ion-dissociative functional compound may be prepared by the first production method, in which $C_6F_6$ and/or $CS_2$ may be employed as solvents in the step to give $C_m-(CF_2-SO_2F)_n$. $C_6F_6$ functions as a good solvent for $C_m-(CF_2-SO_2F)_n$ and $CS_2$ functions as a good solvent for spherical carbon molecules $C_m$, such as fullerene molecules.

The above-mentioned compound $C_m-(CF_2-SO_2F)_n$ should preferably be hydrolyzed under a basic condition to give an ion-dissociative functional compound represented by the chemical formula 2 below.

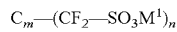

Chemical formula 2

(where m is a natural number for carbon atoms to form a spherical carbon molecule; n is a natural number; and $M^1$ denotes an alkali metal atom.)

In addition, the ion-dissociative functional compound represented by the chemical formula 2 above may be changed into a proton-dissociative functional compound represented by the chemical formula 3 below by replacing the cation of the alkali metal atom $M^1$ with a hydrogen ion.

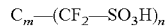

Chemical formula 3

(where m is a natural number for carbon atoms to form a spherical carbon molecule; and n is a natural number.)

According to the present invention, the ion-dissociative functional compound may be prepared by the second production method, in which $C_6F_6$ and/or $CS_2$ may be employed as solvents in the step to give $C_m-(CF_2-SO_2F)_n$. As aforesaid, $C_6F_6$ functions as a good solvent for $C_m-(CF_2-SO_2F)_n$ and $CS_2$ functions as a good solvent for spherical carbon molecules $C_m$, such as fullerene molecules.

Also, the foregoing compound $C_m-(CF_2-SO_2F)_n$ may be changed into an ion-dissociative functional compound having the linkage represented by the chemical formula 6 below by reaction with the compound represented by the chemical formula 5 below.

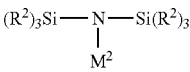

Chemical formula 5

(where $M^2$ denotes a hydrogen atom, an alkali metal atom, or $-Si(R^2)_3$, with $R^2$ being an alkyl group.)

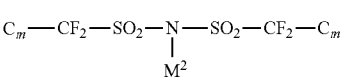

Chemical formula 6

(where m is a natural number for carbon atoms to form a spherical carbon molecule; and $M^2$ denotes an alkali metal atom.)

Subsequently, the ion-dissociative functional compound having the linkage represented by the chemical formula 6 above should preferably be changed into a proton-dissociative functional compound represented by the chemical formula 7 below by replacing the cation of the alkali metal atom $M^2$ with a hydrogen ion.

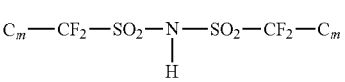

Chemical formula 7

(where m is a natural number for carbon atoms to form a spherical carbon molecule.)

The second ionic conductor according to the present invention should preferably have the fullerene molecule $C_f$ in which f=36, 60, 70, 76, 78, 80, 82, 84, and so on. The fullerene of $C_{60}$ or $C_{70}$ is more desirable. It is readily available at the present time and it is produced at a low cost because of its very high yields. In addition, its uniform shape leads to compact packing and permits ion-dissociative groups to densely attach to its surface.

In addition, at least one of the above-mentioned ion-dissociative group (Gp3) should be any one of proton-dissociative ones selected from the group consisting of hydrogensulfate ester group (—OSO$_2$OH), sulfonic acid group (—SO$_2$OH), dihydrogen phosphate ester group (—OPO(OH)$_2$), hydrogen phosphate ester group (—OPO(OH)—), phosphono group (—PO(OH)$_2$), carboxyl group (—COOH), sulfoneamide group (—SO$_2$—NH$_2$), sulfoneimide group (—SO$_2$—NH—SO$_2$—), methanedisulfonyl group (—SO$_2$—CH$_2$—SO$_2$—), carboxamide group (—CO—NH$_2$), and carboximide group (—CO—NH—CO—). These functional groups contain hydrogen that readily releases itself in the form of proton. Therefore, they are the desirable proton-dissociative functional groups.

The functional groups as represented above are proton-dissociative ones; however, they may have the hydrogen ion replaced by a cation, so that they function as ion-dissociative ones to release the cation. The cations may be those of alkali metal atoms. They are exemplified by lithium ions, sodium ions, potassium ions, rubidium ions, and cesium ions.

The above-mentioned fullerene molecules may be in polymer form in which they are connected to one another by a linkage group containing a sulfoneamide group as represented by the chemical formula 8 below.

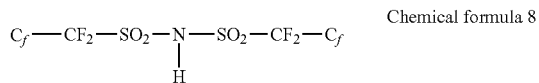

Chemical formula 8

(where C$_f$ denotes the above-mentioned fullerene molecule.)

In the case where the above-mentioned ion-dissociative group (Gp3) is a divalent one (such as sulfoneimide group —SO$_2$—NH—SO$_2$—) which combines with two carbon atoms through two bonding hands, fullerene molecules are connected to one another through the ion-dissociative group (Gp3). The thus polymerized fullerene derivative retains its low water solubility (which leads to high ionic conductivity and high water resistance) even though more ion-dissociative groups (Gp3) are introduced into one fullerene molecule to increase the ionic conductivity.

For the above-mentioned fullerene polymer to have increased ionic conductivity, it should preferably have, in addition to the above-mentioned linking group, a proton-dissociative group selected from the group consisting of hydrogensulfate ester group (—OSO$_2$OH), sulfonic acid group (—SO$_2$OH), dihydrogen phosphate ester group (—OPO(OH)$_2$), hydrogen phosphate ester group (—OPO(OH)—), phosphono group (—PO(OH)$_2$), carboxyl group (—COOH), sulfoneamide group (—SO$_2$—NH$_2$), sulfoneimide group (—SO$_2$—NH—SO$_2$—), methanedisulfonyl group (—SO$_2$—CH$_2$—SO$_2$—), carboxamide group (—CO—NH$_2$), and carboximide group (—CO—NH—CO—). These functional groups contain hydrogen that readily releases itself in the form of proton. Therefore, they are the desirable proton-dissociative functional groups.

The functional groups as represented above are proton-dissociative ones; however, they may have the hydrogen ion replaced by a cation, so that they function as ion-dissociative ones to release the cation. The cations may be those of alkali metal atoms. They are exemplified by lithium ions, sodium ions, potassium ions, rubidium ions, and cesium ions.

The above-mentioned ionic conductor may be made into a film after mixing or compounding with a polymeric binder. The polymeric binder may be a material having low electron conductivity, such as polyvinylidene fluoride, copolymer of polyvinylidene fluoride and hexafluoropropene, polyfluoroethylene, polyvinyl alcohol, polycarbonate, and polyphenylene oxide. Additional film-forming materials include polybenzimidazole and polyamideimide, which are solvent-soluble heat-resistant resins.

The electrochemical device according to the present invention should have the above-mentioned ionic conductor in the form of film with a thickness of 20 µm to 30 µm.

The above-mentioned ionic conductor should be a proton conductor as a constituent of fuel cells. In this case, the ionic conductor should be in the form of film thick enough to have the self-humidifying properties. It may also be used as a constituent of fuel cells for hydrogen or methanol.

The first and second ionic conductors according to the present invention may be produced by a modified method, with —SO$_2$F replaced by —SO$_2$Cl, —SO$_2$Br, or —SO$_2$I.

Figure 1B:
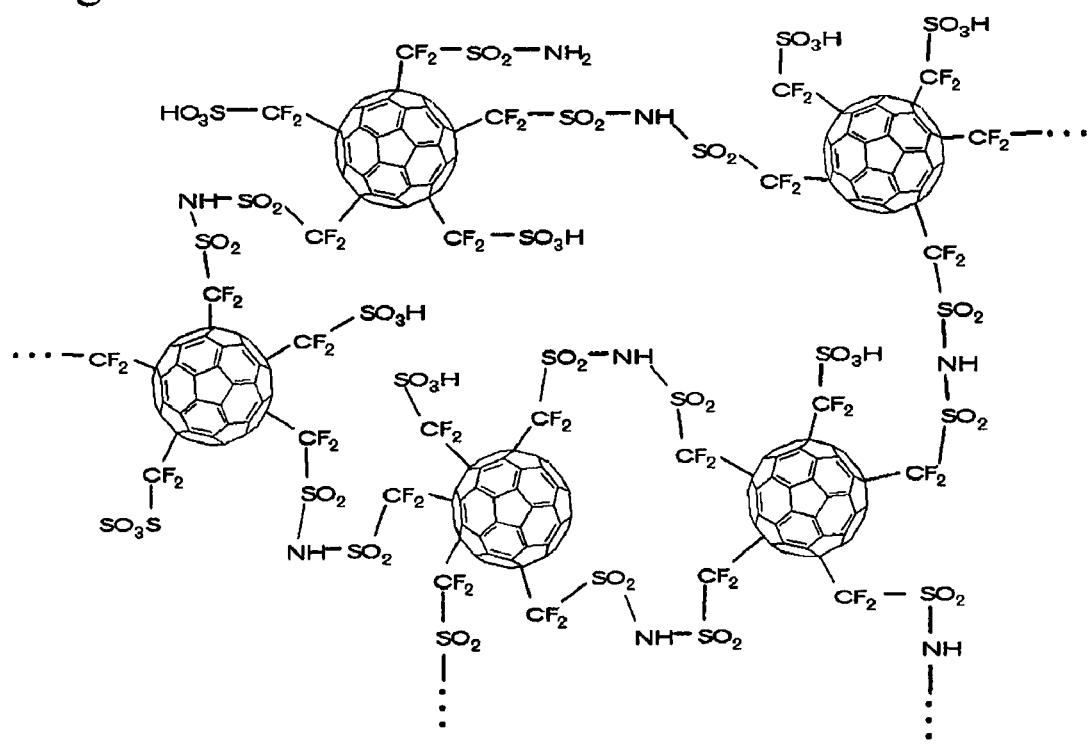
Figure 2:
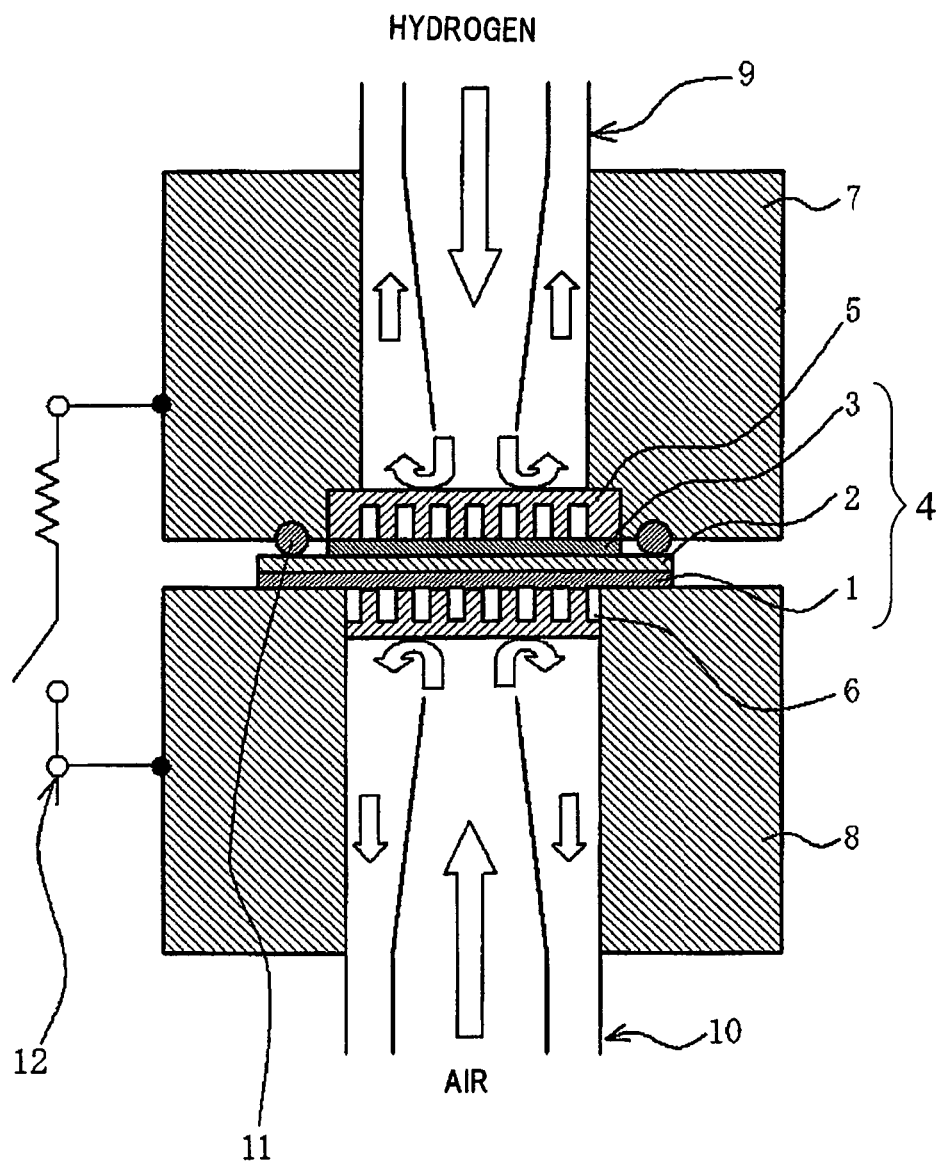
FIG. 2 is a schematic sectional view showing the structure of the fuel cell according to a preferred embodiment of the present invention.
Figure 3A:
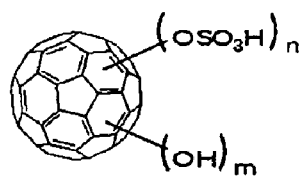
FIGS. 3A to 3D show the examples of the fullerene derivatives having proton conductivity which are cited in Japanese Patent Application No. 2002-28642.
Figure 3B:
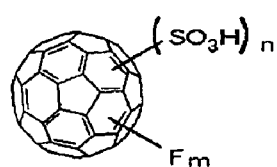
Figure 3C:
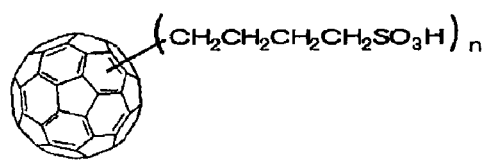
Figure 3D:
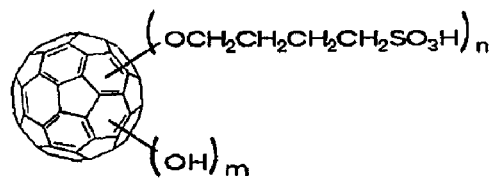

The following illustrates, with reference to FIGS. 1A and 1B and FIG. 2, a fuel cell as an example of the electrochemical device pertaining to a preferred embodiment of the present invention.

FIGS. 1A and 1B are schematic diagrams showing the structure of the proton-dissociative functional compound according to the present invention, which is derived from fullerene monomer (FIG. 1A) or fullerene polymer (FIG. 1B) by the method illustrated in Examples 1 and 2 mentioned later.

The proton-dissociative functional compound shown in FIG. 1A is composed of fullerene C$_{60}$ and about ten sulfonic acid groups —SO$_3$H as proton-dissociative groups, each attached thereto through a difluoromethylene group —CF$_2$—. The proton-dissociative functional compound shown in FIG. 1B is composed of fullerene C$_{60}$ molecules which are three-dimensionally jointed together through —CH$_2$—SO$_2$—NH—SO$_2$—CF$_2$— as the linking group. It contains, in addition to sulfonic acid groups —SO$_3$H, sulfoneimide groups —SO$_2$—NH—SO$_2$— and sulfoneamide groups —SO$_2$—NH$_2$ as the proton-dissociative groups.

FIG. 2 is a schematic sectional view showing the structure of the fuel cell. There is shown the proton conductor 2 in the form of thin film as the ionic conductor according to the present invention. To both sides of the proton conductor 2 are attached the fuel electrode 3 and the oxygen electrode 1, together with an electrode catalyst (not shown). These constituents form the membrane-electrode assembly (MEA) 4. The MEA 4 is held between the cell's upper half 7 and the cell's lower half 8, which are built into the fuel cell.

The cell's upper half 7 and the cell's lower half 8 are provided with the gas supply pipes 9 and 10, respectively. The gas supply pipe 9 feeds hydrogen and the gas supply pipe 10 feeds air or oxygen. Each gas is fed to the fuel electrode 3 and the oxygen electrode 1 through the gas feeders 5 and 6, respectively, each having a sparger (not shown). The gas feeder 5 is electrically connected to the fuel cell electrode 3 and the cell's upper half 7. The gas feeder 6 is electrically connected to the fuel cell electrode 1 and the cell's lower half 8. The cell's upper half 7 is provided with the O-ring 11 to prevent leakage of hydrogen gas.

The fuel cell generates electricity when the external circuit 12 connected to the cell's upper half 7 and the cell's lower half 8 is closed while it is being fed with the above-mentioned gases. Hydrogen becomes oxidized on the surface of the fuel electrode 3 to give electrons to the fuel cell electrode 3 by the chemical reaction represented by the formula (1) below.

$$2H_2 \rightarrow 4H^+ + 4e^- \qquad (1)$$

The resulting hydrogen ions H$^+$ migrate to the oxygen electrode 1 through the proton conductor film 2. In the case of fuel cell of direct methanol type, the fuel electrode 3 may be supplied with methanol as fuel.

The hydrogen ions that have moved to the oxygen electrode 1 react with the oxygen being supplied to the oxygen electrode 1 according to the formula (2) below, $$O_2 + 4H^+ + 4e^- \rightarrow 2H_2O \qquad (2)$$

thereby giving water. At this time, oxygen takes electrons from the oxygen electrode 1 so that it is reduced.

The proton conductor film 2 should be sufficiently thin so that it is humidified with the water generated on the oxygen electrode 1 and it exhibits high proton conductivity. For the proton conductor film 2 to be self-humidifiable, its thickness should be no larger than 500 μm.

EXAMPLES

A description is given below about the examples that demonstrate the ion-dissociative functional compound and the method for production thereof according to the present invention. In the examples, the ion-dissociative functional compound was made into an ionic conductor and the latter was examined for decomposition temperature and proton conductivity.

Example 1

Preparation of an Ion-Dissociative Functional Compound of Fullerene Monomer This example demonstrates the synthesis of poly(difluorosulfomethyl)fullerene $C_{60}$ as the proton-dissociative functional compound by the process which consists of reacting fullerene $C_{60}$ with difluoroiodomethanesulfonylfluoride $CF_2ISO_2F$ and hydrolyzing the resulting product.

[Synthesis of Difluoroiodomethanesulfonylfluoride]

The same method as proposed by Chen Qing-Yuu in ACTA. CHIMICA. SINICA., 48 (1990), 596 or by N. D. Volkov et al., in Synthesis, 1979, 972 was followed to synthesize the difluoroiodomethanesulfonylfluoride-I—$CF_2$—$SO_2F$ to be reacted with fullerene $C_{60}$.

Method of Chen Qing-Yuu:

The first step was to synthesize silver difluoro(fluorosulfonyl)acetate from difluoro(fluorosulfonyl)acetic acid according to the reaction formula below.

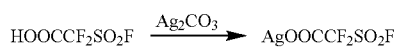

Silver carbonate (5.0 g or 18.2 mmol) was dispersed into diethyl ether at room temperature. To the dispersion was slowly added dropwise with stirring difluoro(fluorosulfonyl)acetic acid (6.5 g or 36.3 mmol). The reactants were kept stirred for about one day at room temperature for their continued reaction. After the reaction was complete, the reaction liquid was filtered to remove unreacted silver carbonate and the filtrate was freed of ether by evaporation. Thus there was obtained a white solid.

This solid was recrystallized from a mixed solvent of diethyl ether and hexane. Thus there was obtained pure silver difluoro(fluorosulfonyl)acetate in the form of white needle crystals. The yield was 9.6 g or 93%. This compound was identified by FT-IR (Fourier transform infrared spectroscopy). The data of FT-IR (Fourier transform infrared spectroscopy) by KBr method is given below. ν [cm$^{-1}$]: 1707, 1690, 1423, 1380, 1232, 1173, 1141, 1021, 809, 758, 610.

The silver difluoro(fluorosulfonyl)acetate was reacted with iodine according to the reaction formula below to synthesize difluoroiodomethanesulfonylfluoride.

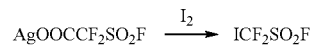

The reaction was carried out by using an apparatus which is provided with a cooling tube in such a way that the reaction liquid in the reaction vessel can be distilled directly. The reaction vessel was charged with the silver difluoro(fluorosulfonyl)acetate (7.2 g or 26.2 mmol) and iodine (10 g or 78.6 mmol). Upon heating at 100° C., the desired difluoroiodomethanesulfonylfluoride distilled through the cooling tube of the distillation apparatus. The distillate was collected. The yield was 3.3 g or 48%. This product was identified by IR and $^{13}$C-NMR and $^{19}$F-NMR (nuclear magnetic resonance).

Method of N. D. Volkov et al.:

The first step was to react silver difluoro(fluorosulfonyl)acetate with iodine to give difluoroiodomethanesulfonylfluoride according to the reaction formula below.

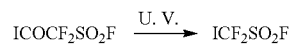

A quartz flask of eggplant shape was charged with difluoro(fluorosulfonyl)acetyl iodide (14.3 g or 50 mmol), followed by irradiation with UV light of mercury lamp for 5 hours at room temperature. The reaction liquid was distilled to give the desired difluoroiodomethanesulfonylfluoride in pure form. The yield was 8.2 g or 63%. This product was identified by IR and $^{13}$C-NMR and $^{19}$F-NMR.

FT-IR (KBr) ν [cm$^{-1}$]: 1460, 1240, 1160, 1120, 930, 890, 810.

$^{13}$C-NMR (CDCl$_3$) [ppm]: 115

$^{19}$F-NMR (CDCl$_3$, C$_6$F$_6$ reference) [ppm]: 113, 192

[Synthesis of Poly(Difluorosulfomethyl)Fullerene]

The desired product was prepared by reacting fullerene $C_{60}$ with difluoroiodomethanesulfonylfluoride $CF_2ISO_2F$ (prepared as mentioned above) and hydrolyzing the reaction product, as explained in the following three steps.

The First Step:

The first step is intended for reaction to introduce sulfonylfluoride groups into fullerene $C_{60}$, thereby giving a first reaction product represented by the general formula $C_{60}$—$(CF_2—SO_2F)$ (where n is about 10), according to the reaction formula below. The first reaction product is a mixture of compounds differing in the number (n) and position of the functional groups introduced. (The same shall apply hereinafter.)

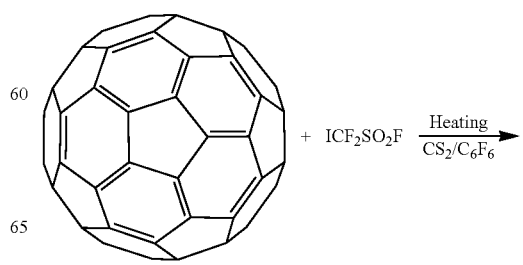

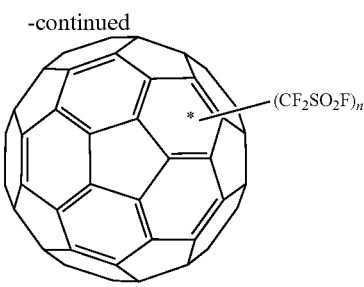

Fullerene $C_{60}$ (0.1 g) and I—$CF_2$—$SO_2F$ (0.43 g) were dissolved in 20 mL of mixed solvent of $C_6F_6$ and $CS_2$ (1:1 by volume). I—$CF_2$—$SO_2F$ is a precursor of the ion-conductive functional group, and its amount was 24 times the amount of fullerene (in equivalent).

Upon heating at 200° C. for 94 hours, the solution gave a reaction product as much as 0.22 g, which exceeds 70% of the theoretical yield. Incidentally, the above-mentioned reaction was carried out in an autoclave under pressure because the mixed solvent of $C_6F_6$ and $CS_2$ boils at about 50° C. under atmospheric pressure.

The precursor of the proton conductive functional group separates into an iodine atom and a radical due to thermal decomposition and the resulting radical attaches itself to the fullerene molecule by its end at which the cleavage of the iodine atom has occurred. The other end ($SO_2F$) of the radical converts into a sulfonic acid group by hydrolysis to be performed subsequently.

The reason why the mixed solvent of $C_6F_6$ and $CS_2$ is used in the above-mentioned reaction is that $C_6F_6$ alone dissolves fullerene only slightly and leaves much fullerene unreacted. $CS_2$ helps increase solubility. On the other hand, it is possible to separate the first reaction product from unreacted fullerene by using $C_6F_6$ which dissolves the former.

The solvent for reaction is not limited to $C_6F_6$ and $CS_2$; it includes aromatic solvents (such as benzene, dichlorobenzene, nitrobenzene, and toluene) and halogenated hydrocarbon solvents (such as carbon tetrachloride, tetrachloroethane, tetrachloroethylene, and trichloroethylene). The former readily dissolve fullerene and the latter are suitable for ordinary radical reactions.

The reaction temperature and time are not limited to those mentioned above. They should be properly changed according to the situation. The reaction time should be set short or long according as the reaction temperature rises or drops. In general, reactions at higher temperatures increase the number of precursors of proton conductive functional groups to be introduced into each fullerene molecule. The result is that the proton conductor has more proton conductive functional groups and exhibits higher proton conductivity.

The reaction temperature should be lower than a certain level at which the precursor of the proton conductive functional group considerably decomposes to give a large amount of decomposition products incapable of reaction with fullerene. In other words, an adequate reaction temperature should be high enough to maximize the number of the precursors of the proton conductive functional groups to be introduced into fullerene but low enough to minimize the side reaction of the precursor molecules while allowing the reaction with fullerene to proceed smoothly. To be concrete, the desirable reaction temperature in this example is about 150 to 240° C. for the reaction time of about 100 hours.

The reaction may be accelerated by using light energy in place of or in addition to heating. This object is achieved by irradiation with visible light or UV light. Any other energy sources than heat may be employed for activation.

The reaction in this example left about 1 to 10% of fullerene unreacted. Unreacted fullerene and undesirable by-products insoluble in solvents should be filtered off as soon as they occur.

The Second Step:

In the second step, the first reaction product was reacted with an alkaline aqueous solution of sodium hydroxide (NaOH) or potassium hydroxide (KOH). This reaction hydrolyzes the sulfonylfluoride group into a second reaction product represented by the general formula of $C_{60}$—($CF_2$—$SO_3Na$)$_n$ (where n is about 10), according to the reaction formula below.

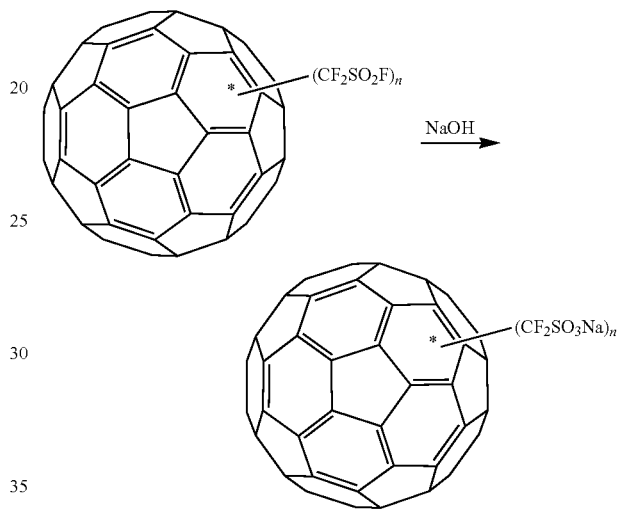

This step should be carried out in an aqueous solution of NaOH mixed with $C_6F_6$ and THF (tetrahydrofuran) so that the first reaction product is hydrolyzed.

$C_6F_6$ added to the aqueous solution helps dissolve the first reaction product (in a dry state) which is only slightly soluble in water and THF. The amount of $C_6F_6$ is not specifically restricted so long as the first reaction product is entirely dissolved.

THF added to the aqueous solution enhances the interfacial activity and accelerates the reaction. Without THF, the NaOH aqueous solution phase is completely immiscible with the $C_6F_6$ solvent phase dissolving the first reaction product. The reaction in this state does not proceed despite stirring. A small amount of THF makes the water phase miscible with the $C_6F_6$ solvent phase, thereby causing the reaction to proceed at once. However, an excess amount of THF prevents the separation of the water phase and the $C_6F_6$ solvent phase. This makes it necessary to remove $C_6F_6$ by using an evaporator in the step of recovering the second reaction product after the reaction. Thus, an adequate amount of THF should be used.

The foregoing was proved by the fact that when 0.2 g of the first reaction product was dissolved in a mixed solvent composed of 5 mL of $C_6F_6$ and 50 mL of THF and the resulting solution was given 10 mL of 1 M NaOH aqueous solution with stirring for hydrolysis, the resulting hydrolyzate moved from the organic phase to the aqueous phase.

After the reaction, excess NaOH was removed from the aqueous phase by silica gel chromatography eluted with a 1:1 mixed solvent of water and THF. Thus there was obtained the second reaction product in purified form.

Since 1 mol of NaOH is necessary to hydrolyze 1 mol of sulfonylfluoride group —$SO_2F$, the minimum amount of NaOH necessary to hydrolyze all the sulfonylfluoride groups introduced into fullerene is 10 times the amount of fullerene (or 10 equivalents of NaOH for 1 equivalent of fullerene). Usually more than the minimum amount of NaOH is used to completely hydrolyze sulfonylfluoride groups.

The NaOH aqueous solution used for hydrolysis contains by-products and excess NaOH in addition to the second reaction product, and hence it is necessary to remove NaOH before the second reaction product is recovered from the aqueous solution by means of silica gel chromatography mentioned above. For efficient removal of NaOH, it is desirable to use a mixed solvent of water and THF as an eluent. Because of its high polarity, water used alone as an eluent gradually removes NaOH which has once been adsorbed to silica gel and the resulting eluate becomes to contain NaOH. By contrast, THF makes the eluent to decrease in polarity and hence keeps NaOH adsorbed to silica gel and prevents NaOH from entering the eluate.

In this way it is possible to obtain a neutral solution (eluate) containing only the second reaction product which is extremely water-soluble. At this point, the neutral solution should be freed of the solvent (THF and water) by using an evaporator under reduced pressure.

The Third Step:

The third step is intended to replace the alkali metal ions (indicated by $Na^+$ below) in the second product with protons as shown below to give the third reaction product represented by the general formula $C_{60}$—$(CF_2$—$SO_3H)_n$ (where n is about 10), which is the desired proton-dissociative functional compound.

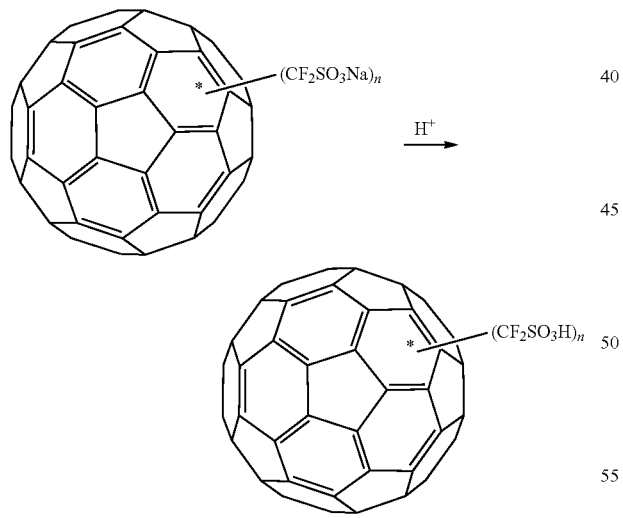

After being freed of solvent (water and THF) as mentioned above, the second reaction product is dissolved in water. The resulting aqueous solution is poured into a column filled with a proton-substituted cation exchange resin. During passage through the column, the second reaction product has sodium ions ($Na^+$) replaced by protons. Thus there is obtained the proton-dissociative functional compound in the eluate.

Incidentally, protonization may also be accomplished by using an inorganic strong acid such as HCl, $H_2SO_4$, $HClO_4$, and $HNO_3$ in place of the above-mentioned cation exchange resin. Any other adequate method may also be employed.

Example 2

Preparation of an Ion-Dissociative Functional Compound of Fullerene Polymer

This example demonstrates the process of synthesizing a solvent-insoluble proton-dissociative functional compound of fullerene polymer by the following four steps. The process consists of reacting fullerene $C_{60}$ with difluoroiodomethane-sulfonylfluoride (in the same way as in Example 1), polymerizing the reaction product by conversion into sulfoneimide, and hydrolyzing the resulting polymer.

The First Step:

The first step is intended for reaction to introduce sulfonylfluoride groups into fullerene $C_{60}$ (in the same way as in Example 1), thereby giving a first reaction product represented by the general formula $C_{60}$—$(CF_2$—$SO_2F)_n$ (where n is about 10), according to the reaction formula below.

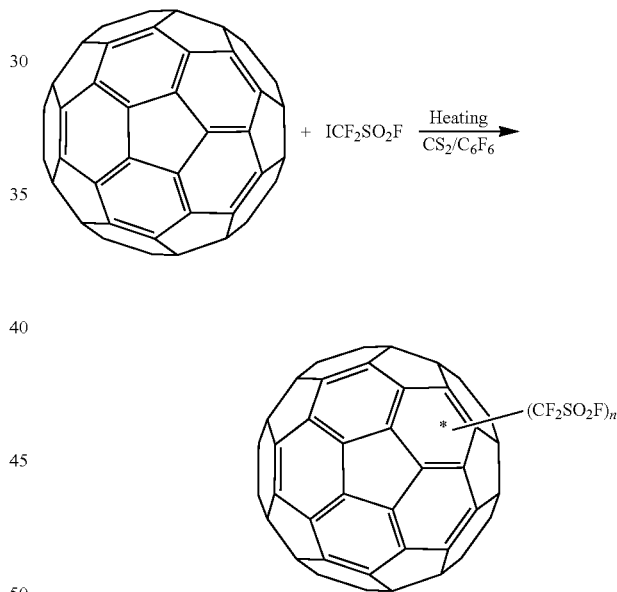

The first step is similar to that in Example 1 except for the fact that the sulfonylfluoride group introduced into the first reaction product is partly used to connect fullerene molecules to each other at the time of conversion into sulfoneimide in the second step. The sulfonylfluoride groups remaining without conversion into sulfoneimide are hydrolyzed in the subsequent step in the same way as in Example 1, so that they are converted into sulfonic acid groups.

The Second Step:

The second step is intended to react the sulfonylfluoride group in the first reaction product with the compound represented by the chemical formula 9 below, thereby linking together fullerene molecules for polymerization, with the sulfonylfluoride group converted into sulfoneimide as shown below.

Chemical formula 9
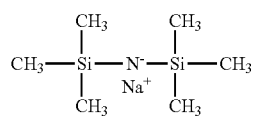
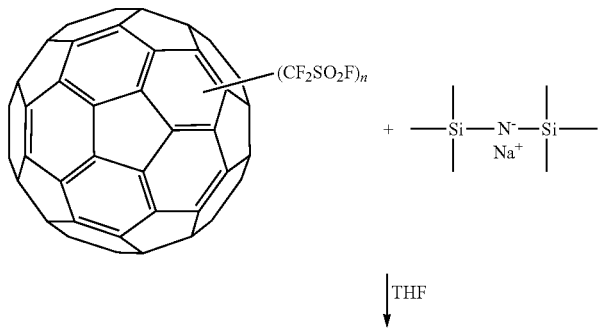
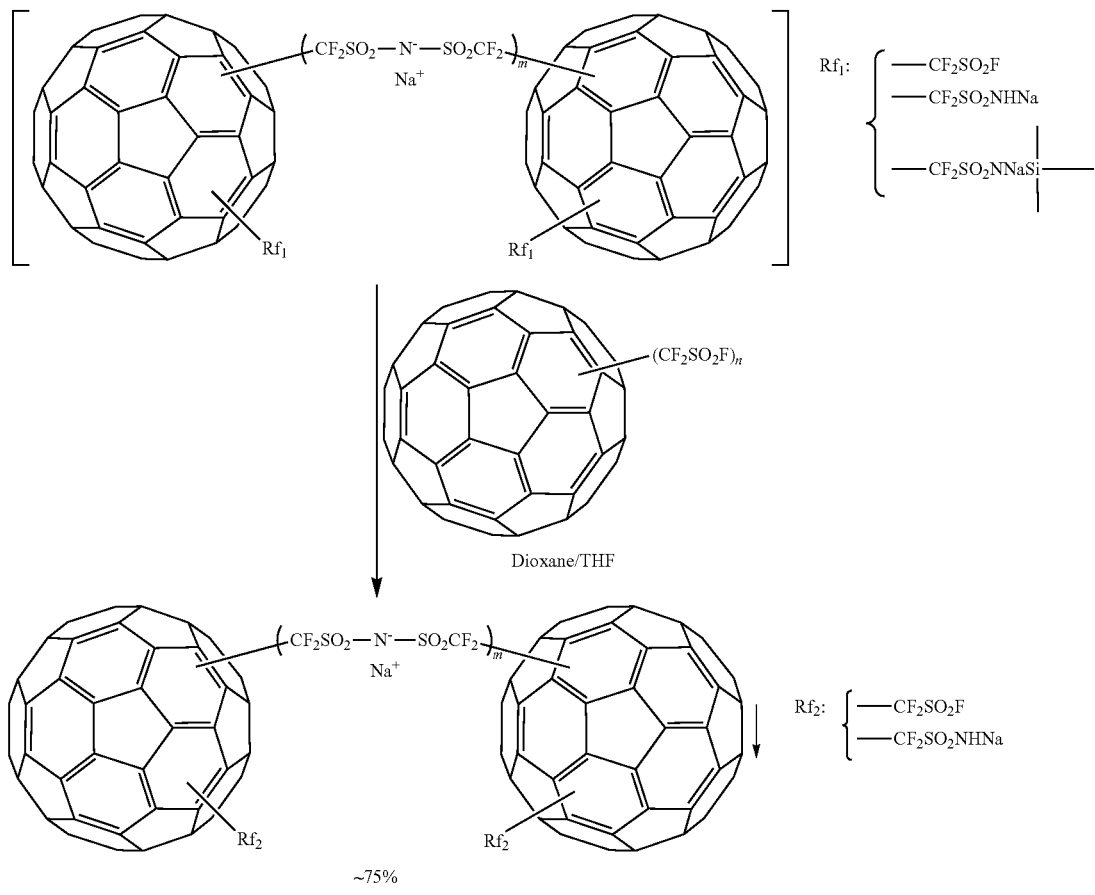

The reaction was carried out as follows. The first reaction product $C_{60}$—$(CF_2SO_2F)_n$ in solid form (0.2 g) was given dropwise 0.5 mL of THF solution containing 1 M of sodium bis(trimethylsilyl)amide with ice cooling in an atmosphere of nitrogen gas. Stirring was continued for 5 hours at room temperature for complete dissolution of $C_{60}$—$(CF_2SO_2F)_n$. With dark brown precipitates separating out, the solution was freed of solvent and the remaining precipitates were dried at 60° C. for 3 hours in vacuum.

The thus obtained solid was dissolved in 8 mL of dioxane added thereto. To the resulting solution was added dropwise from a dropping funnel 0.1 g of the first reaction product $C_{60}$—$(CF_2SO_2F)_n$ dissolved in 2 mL of THF. Reaction was carried out at 80° C. for 18 hours under refluxing. With the solvent removed, the resulting solid was washed with THF and water. Thus there was obtained the second reaction product (about 0.2 g).

The imidizing reagent used in this step also includes the compound represented by the chemical formula 5 below in addition to sodium bis(trimethylsilyl)amide mentioned above. The solvent used in this step also includes non-aqueous organic solvents (such as toluene and hexane) in addition to THF and dioxane. The reaction time is about 1 to 30 hours. Precipitates occur as the reaction proceeds. Heating up to the boiling point of the reaction liquid is desirable to accelerate the reaction which does not readily proceed at room temperature.

Chemical formula 5

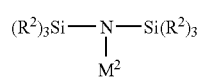

(where $M^2$ denotes H, an alkali metal atom (such as Li, Na, and K), or —$Si(R^2)_3$, with $R^2$ being an alkyl group.)

The Third Step:

The third step is intended to hydrolyze with an alkaline aqueous solution the sulfonylfluoride groups and trimethylsilyl groups remaining unused for polymerization in the second step, as illustrated below.

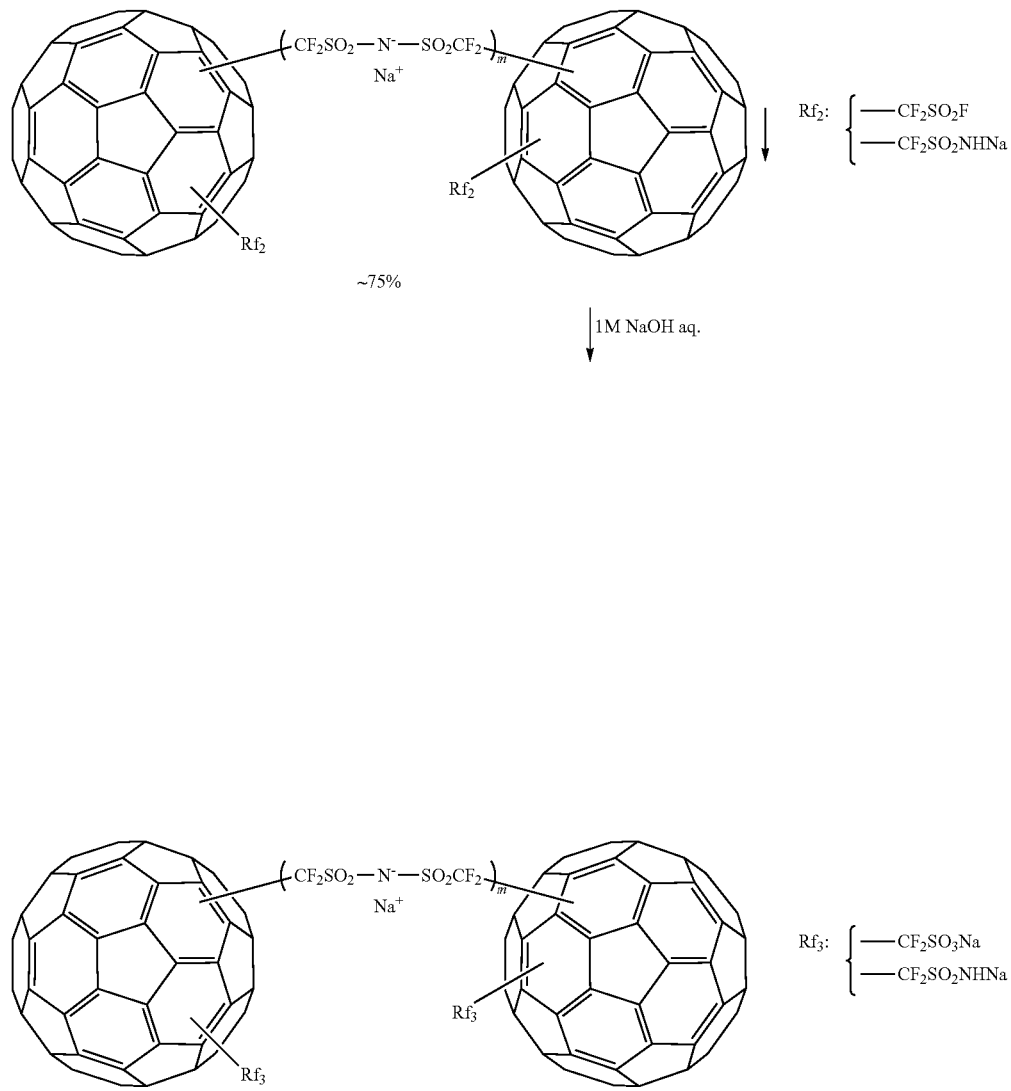

The second reaction product is hydrolyzed by reaction with an alkaline aqueous solution of NaOH or KOH. For example, 0.2 of the second reaction product was dispersed into 50 mL of 1 M NaOH aqueous solution, followed by stirring at room temperature for 16 hours. After filtration and washing with pure water, there was obtained the third reaction product in solid form.

The Fourth Step:

The fourth step is intended to replace the alkali metal ions (indicated by Na$^+$ below) in the third product with protons as shown below to give the desired proton-dissociative functional compound.

Also, if 0.2 g of $C_{60}$—$(CF_2SO_2F)_n$ is reacted with smaller than or equal to 0.01 mL of THF solution of 1 M sodium bis(trimethylsilyl)amide, the sufficiently crosslinked structure is not obtained and the resulting proton-dissociative functional polymer is water-soluble. If the amount of the THF solution is increased, the resulting proton-dissociative functional polymer is water-insoluble. In this way it is possible to make the proton conductor of fullerene polymer water-insoluble by increasing the ratio of the linkage between fullerene molecules even though the proton conductor of fullerene monomer is water-soluble, so long as there are sufficient sites for connection of fullerene nuclei.

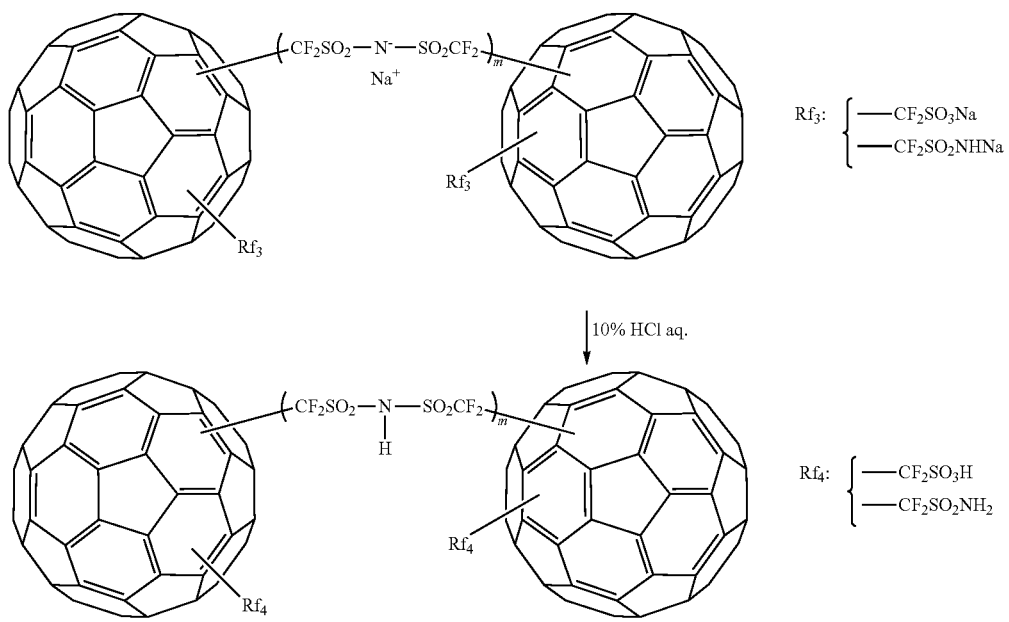

Replacement of cations with protons may be accomplished by using an inorganic strong acid such as HCl, $H_2SO_4$, $HClO_4$, and $HNO_3$. In this example, for instance, the third reaction product in solid form was heated with 10% hydrochloric acid at 60° C. for 12 hours. After filtration and washing with 10% HCl and pure water, there was obtained the desired proton-dissociative functional polymer which is insoluble in solvents.

The sulfonylfluoride groups —$SO_2F$ introduced into fullerene in the first step partly form sulfoneimide groups (as a linkage between fullerene molecules) and partly form sulfonic acid groups by subsequent hydrolysis. Their ratio can be adjusted by controlling the molar ratio of the first reaction product and sodium bis(trimethylsilyl)amide (as an imidizing reagent) in the second step.

In this example, for instance, 0.3 of $C_{60}$—$(CF_2SO_2F)_n$ is reacted with 0.5 mL of THF solution of 1 M sodium bis (trimethylsilyl)amide, so that sulfonylfluoride groups are converted into sulfoneimide groups almost entirely. On the other hand, if 0.2 g of $C_{60}$—$(CF_2SO_2F)_n$ is reacted with 0.1 mL of THF solution of 1 M sodium bis(trimethylsilyl)amide, it is possible to leave intact (without conversion into sulfoneimide) about one half of the —$SO_2F$ groups connecting to the fullerene nuclei without reducing the yield of proton-dissociative functional polymer. The —$SO_2F$ groups remaining unreacted are subsequently converted into sulfonic acid groups —$SO_3H$.

Example 3

Evaluation of Heat Resistance by Analysis of Gas Evolved on Heating

An experiment was carried out to test the samples of proton-dissociative functional compounds obtained in Examples 1 and 2 and the samples of fullerene derivatives (for comparison) shown in FIGS. 3A to 3D for heat resistance by analysis of gas evolved on heating.

To start the experiment, the sample (about 20 mg) was placed in an open vessel. Then, the open vessel holding the sample was placed in a vacuum vessel capable of controlled heating. The vacuum vessel is provided with an RGA (Residual Gas Analyzer) to detect and analyze evolved gas. The RGA is capable of detecting a gas with a molecular weight of 1 to 300.

The vacuum vessel was evacuated to $10^{-7}$ Torr and heated to 500° C. at a heating rate of 4° C./min. The gas that was evolved during heating was detected and analyzed. The analyte was $SO_2$ or $SO_3$ gas arising from decomposition of sulfonic acid groups. The temperature at which these gases are evolved is defined as the decomposition starting temperature, and the temperature at which the maximum amount of gas is evolved is defined as the decomposition peak temperature. Table 1 below shows the results of measurements.

TABLE 1

(Decomposition temperature determined by gas analysis during heating)

| Sample | Decomposition starting temperature (° C.) | Decomposition peak temperature (° C.) |
|---|---|---|
| Example 1 | 175 | 285 |
| Example 2 | 190 | 310 |
| Comparative Example (A) | 110 | 200 |
| Comparative Example (B) | 100 | 225 |

TABLE 1-continued (Decomposition temperature determined by gas analysis during heating)

| Sample | Decomposition starting temperature (° C.) | Decomposition peak temperature (° C.) |
|---|---|---|
| Comparative Example (C) | 110 | 205 |
| Comparative Example (D) | 110 | 210 |

It is noted from Table 1 that the samples from Examples 1 and 2 are by far superior in heat resistance to those from Comparative Examples. In fact, the decomposition starting temperature increased from 100-110° C. for comparative samples to 175° C. or 190° C. for working samples. This temperature rise by far exceeding 100° C. is important in view of the fact that the fuel cell of solid polymer electrolyte type should preferably be run at a temperature close to 100° C. (the boiling point of water) from the standpoint of effective heat utilization and prevention of catalyst poisoning. Therefore, the proton conductor for such fuel cells is required to have a sufficiently long life in such an environment. The samples in Examples 1 and 2 are considered to meet this requirement.

Example 4

Evaluation of Proton Conductivity

An experiment was carried out to test the samples of proton-dissociative functional compounds obtained in Examples 1 and 2 and the samples of fullerene derivatives (for comparison) shown in FIGS. 3A to 3D for proton conductivity inherent in them as proton conductors.

Each of the samples mentioned above was vacuum-dried at room temperature for 12 hours and the resulting power was formed into pellets (about 30 µm thick) by using a tablet machine. At the time of compression, the powder was held between metal electrodes so that the molded pellet (proton conductor) has metal electrodes integrally formed on both sides thereof.

The proton conductivity of the samples was calculated from data obtained by using an impedance analyzer. The results are shown in Table 2. In Table 2, "conductivity in dry state" is the value which was measured when the pellet sample was placed in a vacuum evacuated by a rotary pump. After measurement in dry state, the pellet sample was allowed to stand in an atmosphere of 70% RH for one day. Then, the sample was tested for conductivity. Subsequently, the sample was immersed in water for three days and then tested for conductivity. If the conductivity measured after immersion in water is infinite (as if there is a short circuit between electrodes), it is assumed that the proton conductor has dissolved in water.

TABLE 2

(Proton conductivity calculated from impedance)

| Sample | Conductivity in dry state (S cm$^{-1}$) | Conductivity after standing at 70% RH (S cm$^{-1}$) | Conductivity after immersion in water for three days (S cm$^{-1}$) |
|---|---|---|---|
| Example 1 | $1.5 \times 10^{-3}$ | $3.4 \times 10^{-2}$ | Dissolved |
| Example 2 | $5.5 \times 10^{-4}$ | $8.9 \times 10^{-3}$ | $5.4 \times 10^{-2}$ |
| Comparative Example (A) | $2.5 \times 10^{-3}$ | $3.6 \times 10^{-2}$ | Dissolved |
| Comparative Example (B) | $<10^{-6}$ | $4.0 \times 10^{-3}$ | Dissolved |
| Comparative Example (C) | $<10^{-6}$ | $1.5 \times 10^{-3}$ | Dissolved |
| Comparative Example (D) | $<10^{-6}$ | $1.0 \times 10^{-3}$ | Dissolved |

It is noted from Table 2 that working samples are comparable to or better than comparative samples in proton conductivity. The sample from Example 1 has a high conductivity in its dry state. This is important for the fuel cell to be humidified easily. The sample from Example 2 has an extremely high water resistance. This is also important for application to the direct methanol fuel cell.

As mentioned above, the embodiments and examples of the present invention provide the fullerene-based proton conducting material which has high proton conductivity and exhibits good thermal and chemical stability under the conditions required of electrochemical devices.

The fullerene-based proton conducting material is a new proton conductor of spherical fullerene molecules which possesses the advantage (or stability) of Nafion as the most commonly used proton conductor.

Having an extremely large number of proton-conducting groups per molecule weight, the fullerene-based proton conducting material as mentioned above exhibits high proton conductivity. It also exhibits comparatively low humidity sensitivity if it has acid groups attached to fullerene molecules through fluorinated methylene groups having a short chain. The problem with water-solubility is solved by crosslinking through sulfoneimide the sulfonylfluoride group as the precursor of the proton-dissociative group.

The fullerene-based proton conducting material according to the present invention may be used as a proton exchange membrane to be incorporated into a thermally and chemically stable electrochemical device which is self-humidifiable and capable of start-up in a dry state.

While the invention has been described in its preferred embodiments and examples, it is not limited to them. Obviously, variations and changes may be made without departing from the scope and spirit of the invention.

INDUSTRIAL APPLICABILITY

The present invention may be applied to electrochemical devices, such as fuel cells and sensors, which have an electrochemical reaction unit in which a membrane of ionic conductor is held between a pair of electrodes. The fuel cell according to the present invention has improved performance and low cost because of its higher operating temperature than the conventional fuel cell of solid polymer electrolyte type and its simplified system for water control of membrane. In particular, the present invention is applicable most suitably to the fuel cell of direct methanol type which is difficult to realize with the conventional proton conducting membrane.

The ion-dissociative functional compound according to the present invention is constructed such that the ion-dissociative group (Gp1) does not combine directly with the spherical carbon molecules $C_m$, such as fullerene nuclei having unsaturated bonds but combines indirectly with the spherical carbon molecules $C_m$ through a difluoromethylene group. This difluoromethylene group is derived from a methylene group (which is a basic skeleton of a saturated hydrocarbon) by substitution of its hydrogen atom with a fluorine atom. It is chemically inert and has enhanced heat resistance. For this reason, the ion-dissociative functional compound keeps the ion-dissociative group (Gp1) unaffected by the unsaturated bond. Moreover, it is most thermally and chemically stable among the derivatives of spherical carbon molecules $C_m$ having the ion-dissociative group (Gp1) because the difluoromethylene group is chemically inert and has high heat resistance.

The first ionic conductor according to the present invention is thermally and chemically stable because it is composed of the ion-dissociative functional compound. Moreover, the first ionic conductor densely possesses the ion-dissociative groups (Gp1) because the difluoromethylene group has a minimum size as a spacer group and hence a large number of the ion-dissociative groups (Gp1) can be introduced into one spherical carbon molecule $C_m$. Consequently, it exhibits high ion conductivity even under the condition of comparatively low humidity.

The ion-dissociative functional compound assumes a polymer form when the spherical carbon molecules Clare bonded to each other through the ion-dissociative group (Gp2). This holds true in the case where the ion-dissociative group (Gp2) has a divalent or multivalent group, such as sulfoneimide group —SO$_2$—NH—SO$_2$—, which is capable of bonding two carbon atoms through two bonding hands. The ion-dissociative functional compound in a polymer form remains low in water solubility even though the number of the ion-dissociative groups (Gp1 or Gp2) to be introduced into one spherical carbon molecule $C_m$ is increased to enhance ionic conductivity. Consequently, the ionic conductor composed of the polymerized ion-dissociative functional compound exhibits high water resistance.

According to the present invention, the first and second ion-dissociative functional compounds are produced respectively from the monomer and polymer of spherical carbon molecules $C_m$. Their production method is easy to perform in high yields because it consists of simple reactions of addition, hydrolysis, and substitution.

The second ionic conductor according to the present invention is a fullerene derivative in which the ion-dissociative group (Gp3) combines indirectly with the fullerene nucleus through the difluoromethylene group. Therefore, it keeps the ion-dissociative group (Gp3) unaffected by the unsaturated bond, and it is thermally and chemically stable because the difluoromethylene group is chemically inert and has high heat resistance. Moreover, the second ionic conductor densely possesses the ion-dissociative groups (Gp3) because the difluoromethylene group has a minimum size as a spacer group. Consequently, it exhibits high ion conductivity even under the condition of comparatively low humidity.

The electrochemical device according to the present invention remains thermally and chemically stable in a broad temperature range because it is constructed such that the ionic conductor held between the first and second electrodes conducts ions from the first electrode to the second electrode. In addition, it achieves high ion conductivity under the condition of comparatively low humidity, and it starts up rapidly even in a dry state.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. An ionic conductor comprising a composition including an ion-dissociative functional compound consisting of a linkage structure represented by a chemical formula as follows:

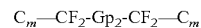

$$C_m\text{—}CF_2\text{-}Gp_2\text{-}CF_2\text{—}C_m$$

wherein $C_m$ is a fullerene molecule, and wherein $Gp_2$ is an ion-dissociative group and is a proton-dissociative group selected from the group consisting of sulfoneamide group (—SO$_2$—NH$_2$), sulfoneimide group (—SO$_2$—NH—SO$_2$—), methanedisulfonyl group (—SO$_2$—CH$_2$—SO$_2$—), and carboximide group (—CO—NH—CO—).

2. The ionic conductor according to claim 1, wherein the ionic conductor is configured as a film having a thickness ranging from 20-30 μm.

* * * * *